United States Patent

Rogers et al.

[11] Patent Number: 5,989,026
[45] Date of Patent: Nov. 23, 1999

[54] CERAMIC TWO-PIECE DENTAL ABUTMENT

[75] Inventors: Dan Paul Rogers, Royal Palm Beach; Gale R. Brown, Palm City, both of Fla.; Daniel Y. Sullivan, McLean, Va.

[73] Assignee: Implant Innovations, Inc., Palm Beach Gardens, Fla.

[21] Appl. No.: 09/179,493

[22] Filed: Oct. 26, 1998

Related U.S. Application Data

[63] Continuation-in-part of application No. 08/729,869, Oct. 15, 1996, Pat. No. 5,829,977, and a continuation-in-part of application No. 08/451,083, May 25, 1995, Pat. No. 5,725,375
[60] Provisional application No. 60/005,702, Oct. 17, 1995, abandoned.
[51] Int. Cl.⁶ .............................. A61C 13/12; A61C 8/00
[52] U.S. Cl. ........................................ 433/172; 433/173
[58] Field of Search .................................. 433/172, 173, 433/174

[56] References Cited

U.S. PATENT DOCUMENTS

| | | | |
|---|---|---|---|
| 2,721,387 | 10/1955 | Ashuckian | 32/10 |
| 3,958,471 | 5/1976 | Müller | 82/1 |
| 4,011,602 | 3/1977 | Rybicki et al. | 433/173 |
| 4,177,562 | 12/1979 | Miller et al. | 433/174 |
| 4,259,072 | 3/1981 | Hirabayashi et al. | 433/173 |
| 4,547,157 | 10/1985 | Driskell | |
| 4,560,353 | 12/1985 | Schulte et al. | 433/173 |
| 4,575,340 | 3/1986 | Lustig | 433/173 |
| 4,624,673 | 11/1986 | Meyer | |
| 4,713,004 | 12/1987 | Linkow et al. | |
| 4,738,623 | 4/1988 | Driskel | 433/173 |
| 4,746,293 | 5/1988 | Lundgren et al. | 433/173 |
| 4,758,161 | 7/1988 | Niznick | 433/173 |
| 4,772,204 | 9/1988 | Söderberg | 433/174 |
| 4,824,372 | 4/1989 | Jörnéus et al. | 433/174 |
| 4,846,683 | 7/1989 | Lazzara et al. | 433/173 |
| 4,850,870 | 7/1989 | Lazzara et al. | 433/174 |
| 4,850,873 | 7/1989 | Lazzara et al. | 433/220 |
| 4,854,872 | 8/1989 | Detsch | 433/173 |
| 4,856,994 | 8/1989 | Lazzara et al. | 433/173 |
| 4,872,839 | 10/1989 | Brajnovic | |
| 4,904,187 | 2/1990 | Zingheim | 433/173 |
| 4,955,811 | 9/1990 | Lazzara et al. | 433/173 |
| 4,978,640 | 12/1990 | Kelly | 501/32 |
| 4,988,297 | 1/1991 | Lazzara et al. | |
| 4,988,298 | 1/1991 | Lazzara et al. | 433/173 |
| 5,000,686 | 3/1991 | Lazzara et al. | 433/174 |
| 5,006,069 | 4/1991 | Lazzara et al. | 433/173 |
| 5,015,186 | 5/1991 | Detsch | 433/173 |
| 5,022,860 | 6/1991 | Lazzara et al. | 433/174 |
| 5,030,096 | 7/1991 | Hurson et al. | 433/173 |
| 5,035,619 | 7/1991 | Daftary | 433/173 |
| 5,040,982 | 8/1991 | Stefan-Dogar | 433/169 |
| 5,040,983 | 8/1991 | Binon | 433/173 |
| 5,064,373 | 11/1991 | Staubli et al. | 433/173 |
| 5,071,345 | 12/1991 | Rosen | 433/17 |
| 5,071,351 | 12/1991 | Green, Jr. et al. | 433/173 |
| 5,073,111 | 12/1991 | Daftary | 433/173 |
| 5,082,442 | 1/1992 | Rosen | 433/17 |
| 5,087,200 | 2/1992 | Brajnovic et al. | 433/173 |
| 5,100,323 | 3/1992 | Friedman et al. | 433/173 |
| 5,104,318 | 4/1992 | Piche et al. | 433/174 |
| 5,105,690 | 4/1992 | Lazzara et al. | 81/436 |
| 5,106,300 | 4/1992 | Voitik | 433/173 |
| 5,122,059 | 6/1992 | Durr et al. | 433/173 |
| 5,125,839 | 6/1992 | Ingber et al. | 433/169 |
| 5,135,395 | 8/1992 | Marlin | 433/174 |
| 5,145,371 | 9/1992 | Jörnéus | 433/173 |
| 5,145,372 | 9/1992 | Draftery et al. | 433/173 |
| 5,152,687 | 10/1992 | Amino | 433/173 |
| 5,154,612 | 10/1992 | Carlsson et al. | 433/173 |
| 5,169,308 | 12/1992 | Kvist | 433/173 |
| 5,169,309 | 12/1992 | Staubli et al. | 433/173 |
| 5,188,800 | 2/1993 | Green, Jr. et al. | 422/23 |
| 5,195,892 | 3/1993 | Gersberg | 433/173 |
| 5,197,881 | 3/1993 | Chalifoux | 433/173 |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,246,370 | 9/1993 | Coatoam | 433/173 |
| 5,281,140 | 1/1994 | Niznick | 433/172 |
| 5,282,746 | 2/1994 | Sellers et al. | 433/172 |
| 5,286,195 | 2/1994 | Clostermann | 433/172 |
| 5,292,252 | 3/1994 | Nickerson et al. | 433/173 |
| 5,297,963 | 3/1994 | Daftary | 433/172 |
| 5,316,476 | 5/1994 | Krauser | 433/173 |
| 5,334,024 | 8/1994 | Niznick | 433/173 |
| 5,336,090 | 8/1994 | Wilson, Jr. et al. | 433/172 |

5,989,026
Page 2

| | | | |
|---|---|---|---|
| 5,338,196 | 8/1994 | Beaty et al. | 433/172 |
| 5,344,457 | 9/1994 | Pilliar et al. | 623/16 |
| 5,350,300 | 9/1994 | Gallais | 433/173 |
| 5,362,234 | 11/1994 | Salazar et al. | 433/173 |
| 5,362,235 | 11/1994 | Daftary | 433/173 |
| 5,368,483 | 11/1994 | Sutter et al. | 433/173 |
| 5,417,570 | 5/1995 | Zuest et al. | 433/173 |
| 5,419,702 | 5/1995 | Beaty et al. | 433/214 |
| 5,431,567 | 7/1995 | Daftary | 433/172 |
| 5,433,606 | 7/1995 | Niznick et al. | 433/173 |
| 5,437,551 | 8/1995 | Chalifoux | 433/173 |
| 5,447,435 | 9/1995 | Brodbeck | 433/172 |
| 5,476,382 | 12/1995 | Daftary | 433/172 |
| 5,492,471 | 2/1996 | Singer | 433/172 |
| 5,533,898 | 7/1996 | Mena . | |
| 5,538,426 | 7/1996 | Harding et al. | 433/172 |
| 5,547,377 | 8/1996 | Daftary . | |
| 5,564,924 | 10/1996 | Kwan . | |
| 5,588,838 | 12/1996 | Hansson et al. | 433/173 |
| 5,685,714 | 11/1997 | Beaty et al. | 433/172 |
| 5,829,977 | 11/1998 | Rogers et al. | 433/172 |

FOREIGN PATENT DOCUMENTS

| | | | |
|---|---|---|---|
| 0 320 024 A1 | 6/1989 | European Pat. Off. | A61C 8/00 |
| 0 477 644 A1 | 4/1992 | European Pat. Off. | A61C 8/00 |
| 0 657 146 A1 | 6/1995 | European Pat. Off. | A61C 8/00 |
| 21 14 323 | 10/1971 | Germany . | |
| 21 57 139 | 5/1972 | Germany | A61C 13/26 |
| 27 17 506 A1 | 5/1978 | Germany | A61F 1/100 |
| 32 24 112 A1 | 2/1984 | Germany | A61C 13/30 |
| 35 31 389 A1 | 3/1987 | Germany . | |
| 38 25 601 A1 | 3/1989 | Germany | A61C 13/30 |
| 40 28 855 A1 | 3/1992 | Germany | 433/173 |
| 41 27 839 A1 | 3/1992 | Germany | A61C 8/00 |
| 1570720 A1 | 6/1990 | U.S.S.R. | A61C 13/30 |
| 1 291 470 | 10/1972 | United Kingdom . | |
| 2 213 065 | 8/1989 | United Kingdom | A61C 13/30 |
| WO 85/02337 A1 | 6/1985 | WIPO . | |

OTHER PUBLICATIONS

"1989 Core–Vent Implant Symposium," Core–Vent Corporation, Mar. 1988 (2 pages).

Adell et al., "A 15–year Study of Osseointegrated Implants in the Treatment of the Endentulous Jaw," *Int. J. Oral Surg.*, 1981, pp. 387–416.

Dental Imaging Associates, Inc., et al., The DIA Anatomic Abutment System™, Oct. 1991, pp. 1–10.

DIA™ Dental Imaging Associates, Implamed—The Source, The Anatomical Abutment System, pp. 1–10, Oct. 9, 1991.

"EsthetiCone™ systeM Components," Undated (1 page).

Exhibit A, drawing of a healing abutment.

Exhibit B, assembly drawing of a coping and the component drawings which comprise the coping assembly.

Lewis, S., et al., The "UCLA" Abutment, The International Journal Of Oral & Maxillofacial Implants, vol. 3, No. 3, 1988, pp. 183–189.

Lewis, Steven G., et al., Single Tooth Implant Supported Restorations, The International Journal Of Oral & MaxillofacialImplants, vol. 3, No. 1, 1988, pp. 25–30.

New Bio–Esthetic™ Technique Manual, "Abutment Selection and Modification Guide," Steri–Oss Inc., 1995 (6 pages).

Perri, George, DDS et al., Single Tooth Implants, CDA Journal, vol. 17, No. 3, Mar. 1989.

*Primary Examiner*—John J. Wilson
*Assistant Examiner*—Patrick A. Hilsmier
*Attorney, Agent, or Firm*—Arnold White & Durkee

[57] ABSTRACT

A two-piece abutment system is disclosed. The first part includes a tapering inner surface which is part of a bore extending entirely through the first part. The first part includes a socket for mating with a boss or post on a dental implant. The elongated second part includes a threaded stem for engaging a threaded bore with a dental implant and a post which extends above the first part. The second part extends through the bore of the first part and is screwed into the implant. As the second part is screwed into the implant, a tapering external surface on the post of the second part frictionally locks with the tapering inner surface of the first part. The first part has a metallic core which is surrounded by a ceramic outer portion.

47 Claims, 15 Drawing Sheets

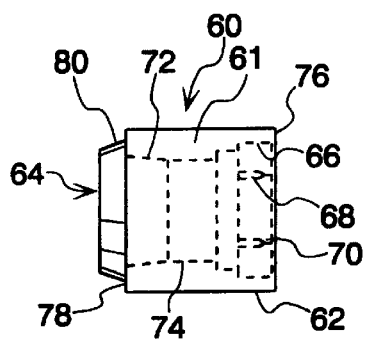
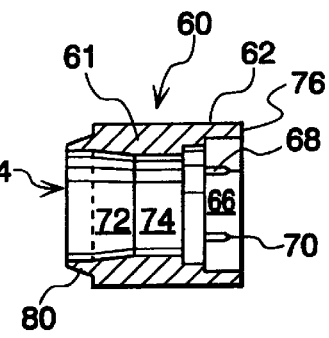
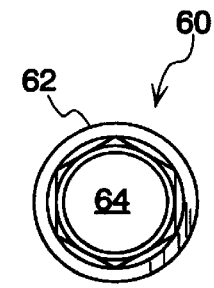
Fig. 7A    Fig. 7B    Fig. 7C
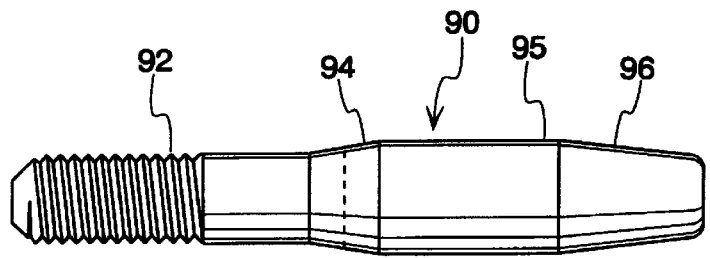
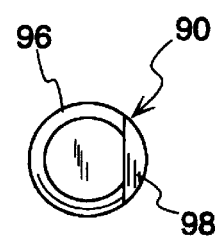
Fig. 8A    Fig. 8B
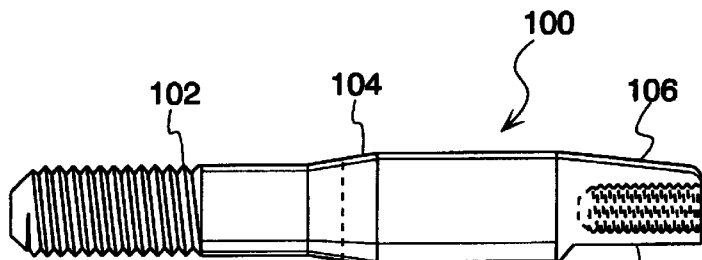
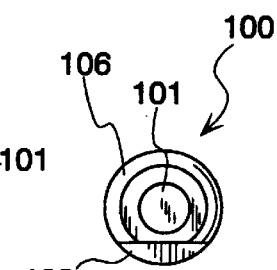
Fig. 9A    Fig. 9B

CERAMIC TWO-PIECE DENTAL ABUTMENT

CROSS REFERENCES TO RELATED APPLICATIONS

This application is a continuation-in-part of application Ser. No. 08/729,869, filed on Oct. 15, 1996, now U.S. Pat. No. 5,829,977 which claims priority to provisional U.S. patent application Ser. No. 60/005,702, filed on Oct. 17, 1995, now abandoned, and U.S. patent application Ser. No. 08/451,083, filed on May 25, 1995, now U.S. Pat. No. 5,725,375.

BACKGROUND OF THE INVENTION

Surgical techniques for support of dental prostheses by means of metallic bone-embedded artificial root fixtures are well known. According to one prior art technique, a titanium bone-embedded implant fixture is interfaced with a metallic abutment post, on which the superstructure is supported. The post has an internally shouldered access bore through which a screw fastener is inserted to actually hold the implant and the post assembled. A number of problems and restrictions are presented however in the attachment of and retention of the superstructures to such abutment posts.

Specifically, the typical superstructures for use with such posts are made of porcelain. The use of a titanium post generally results in a dark, central rod-like shadow, particularly when exposed to high-brightness light, which makes the prosthesis somewhat unattractive and able to be distinguished from a natural tooth. Further, since the materials are different, there are sometimes presented problems with securing of the prosthesis to the support post.

One attempt to solve the attractiveness and securing problems has involved making a support post made entirely of ceramic material, specifically, aluminum oxide. This approach allows direct surface bonding by interaction of a porcelain coping and/or prosthesis to the support post resulting in a secure and almost seamless bond between the prosthetic structure and the support post. While presenting an alternative attraction to the use of a titanium support post, the proposed solution presents a number of previously unanticipated problems.

Ceramic materials generally have a much greater hardness than titanium. When such a support post is used, inevitable rocking of the support post due to, for example, chewing action, causes a high-stress interaction between the metal implant and the ceramic material of the post. Since ceramic is of greater hardness than the titanium implant, it can and does cause damage to the implant. If sufficient damage is caused, eventual surgical intervention is required to remove and replace the titanium implant. In addition, ceramic material is typically not radiopaque. Thus, when examining the juncture between the support post and the titanium implant through conventional dental x-ray imaging, the interface between the two elements is not readily viewable and thus adequate x-ray examination cannot be conducted.

SUMMARY OF THE INVENTION

This specification describes, with references to the accompanying drawings, an improvement in abutments used to attach dental restorations to artificial dental roots such as dental implants. The illustrated abutment has a generally tubular first part which can be fitted through overlying gum tissue and attached non-rotationally to a dental implant. The first part provides a through-passage to a receiving bore in the implant. A second part of the abutment has an attaching stem extending through the through-passage of the first part into the receiving bore and a post protruding supragingivally through the first part from the stem. The post of the second part and the first part have respective male and female interfitting locking tapers which serve to frictionally lock the second part against turning in the first part when the stem is properly engaged in the receiving bore. Typically, the receiving bore is internally threaded and the stem is externally threaded so as to screw into the receiving bore.

In use, the first part is fitted onto the implant and the threaded stem of the second part is screwed into the receiving bore until the male locking taper of the second part engages tightly in the female locking taper of the first part. In this way, the two-piece abutment is effectively attached non-rotationally to the implant.

To provide an abutment that is more aesthetically pleasing, the tubular first part includes a metallic core with a ceramic outer portion. The outer portion, which can be aluminum oxide, is a lighter color than the typical titanium metal used for abutments. Thus, by using the lighter colored ceramic, the gingival tissue remains closer to its natural color than when the darker titanium is used.

The post of the second part may be configured to serve other functions in the dental restoration process. For example, the post may have flat side that allows it to serve as an impression coping. Additionally, the post may have means for fastening other components thereon. For example, a healing cap that encompasses the post may be attached to the post. Alternatively, an impression coping may be attached thereon. Lastly, the post may serve as a structure for supporting both a temporary or permanent dentition.

BRIEF DESCRIPTION OF THE DRAWINGS

In the accompanying drawings:

FIGS. 7A–7C illustrate an alternative first part which has a cylindrical outer surface;

FIGS. 8A–8B illustrate an alternative second part having a flattened side on its post;

FIGS. 9A–9B illustrate an alternative second part having a threaded bore in its post;

DETAILED DESCRIPTION OF THE DRAWINGS

Figure 1:
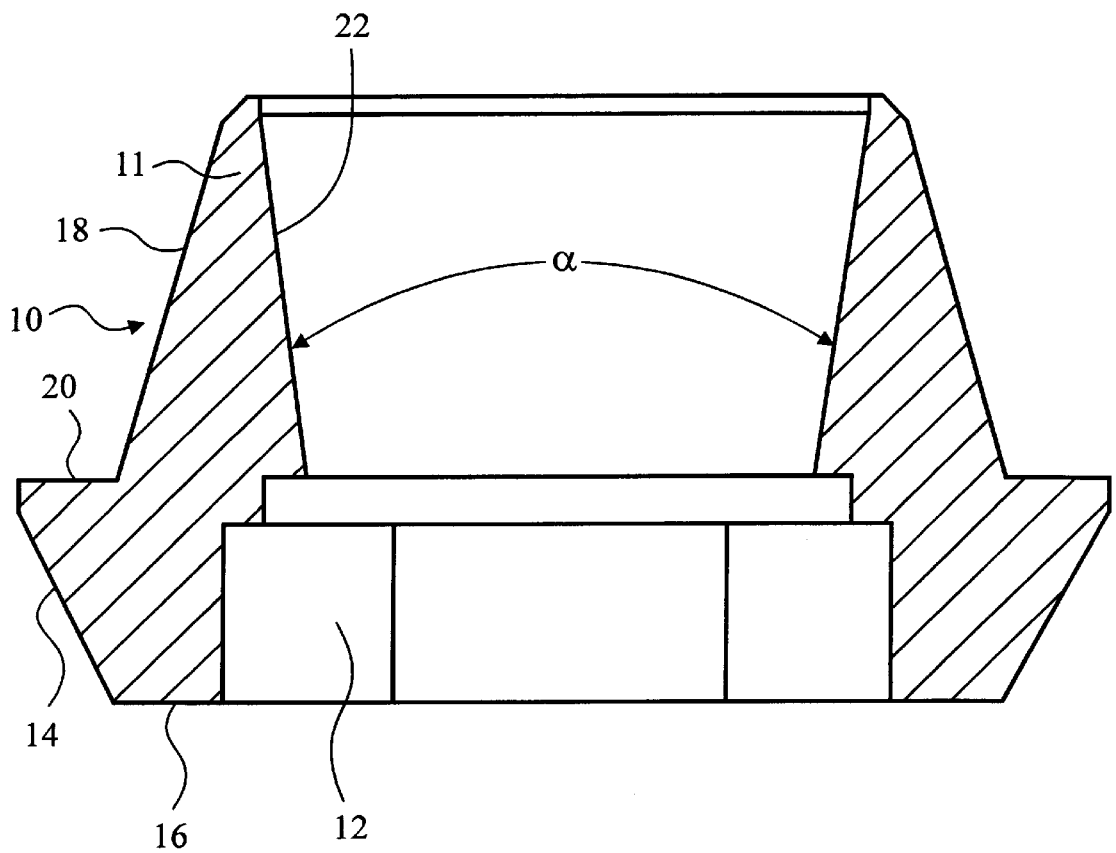
FIG. 1 shows a first part of the two-piece abutment in longitudinal cross-section.

The first part 10 shown in FIG. 1 comprises a tubular body 11 having a socket 12 at its lower section 14. The socket 12 extends upwardly into the body 11 from its lower wall 16 and has a regular polygonal (hexagonal) transverse shape for intermitting non-rotationally on a matching boss of a typical dental implant (illustrated in FIGS. 11–15). Externally, the lower section 14 of the body 11 has an expanding transverse size as it proceeds away from the lower wall 16 and an upper section 18 of contracting transverse size as it proceeds further away from the lower wall 16. Where the lower and uppers sections 14 and 18 are joined, the upper section 18 is smaller transversely than the lower section 14 which provides for a shoulder 20 facing away from the implant. The upper section has a female locking taper 22 which opens into the socket 12. The female locking taper 22 and the socket 12 form a part of a bore through the first part 10. The female locking taper 22 diverges at an angle α which is generally in the range from about 5° to about 20°.

Figure 2:
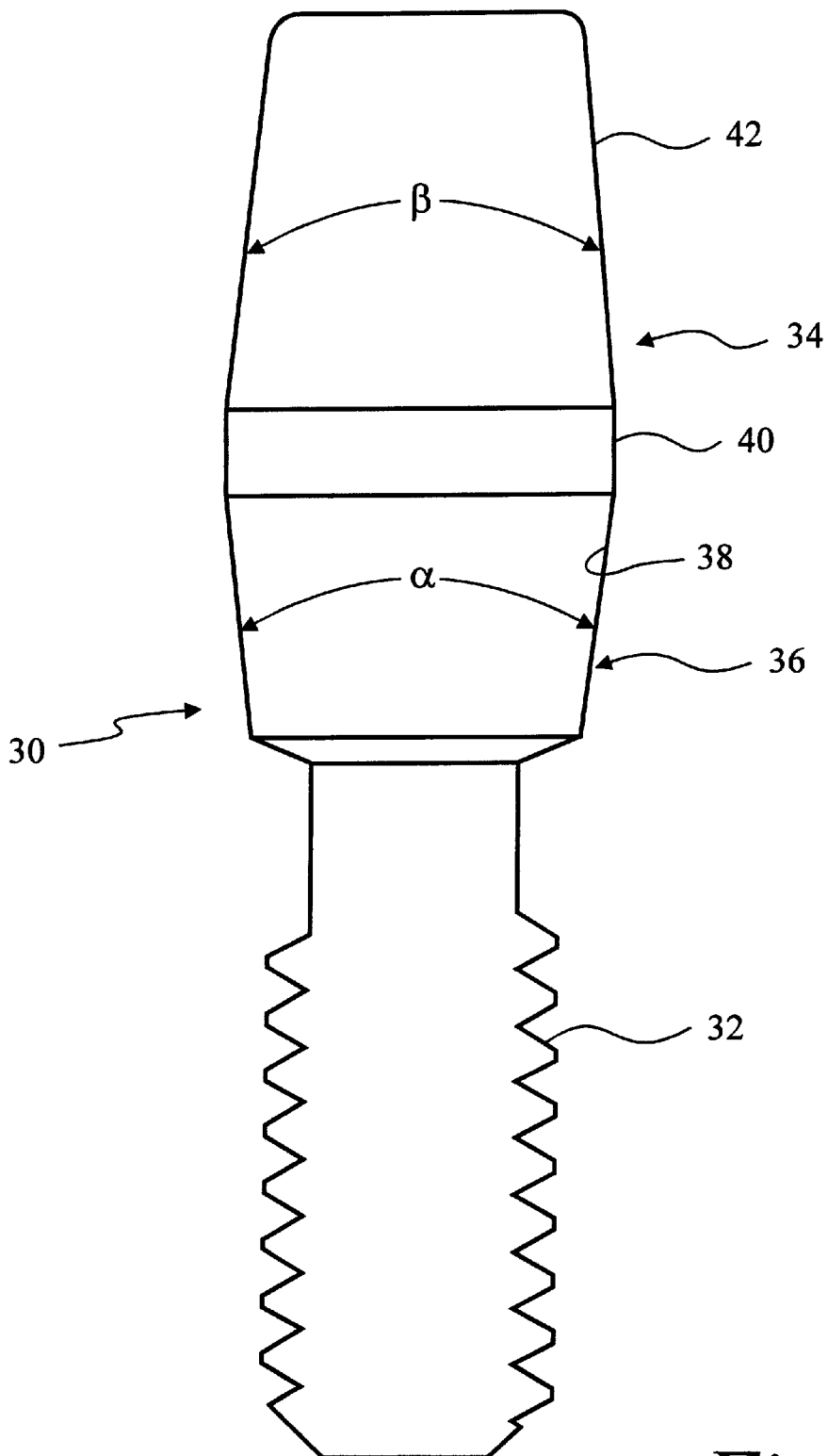
FIG. 2 is a side view of a second part of the two-piece abutment.

The second part 30 shown in FIG. 2 has a threaded stem 32 and a post 34 which is in three sections. A first section 36 has a male locking taper 38 matching the female locking taper 22 of the first part 10. Thus, angle α in the first section 36 is the same as angle α in the female locking taper 22 of the first part 10. An intermediate section 40 is generally cylindrical. A third section 42 has a contracting transverse section and tapers inwardly at an angle β which is typically in the range from about 5° to about 30°. The size of the post 34 may vary based on the patient and the function for which the second part 30 is used. For example, a second part 44 in FIG. 3 has a post with a longer intermediate section 46.

Figure 4:
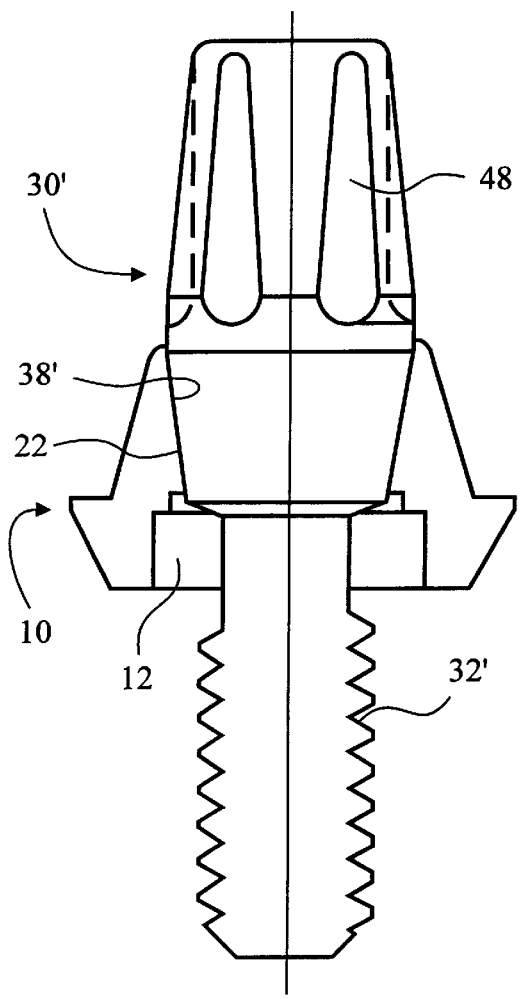
FIG. 4 is a side view of an assembly of a second part having flutes along the post and the first part of FIG. 1.

As can be seen in FIG. 4, the post extends above the first part 10 by an amount at least as large as the height of the first part 10. In some cases, as is shown in FIG. 6, the post extends above the first part 10 by an amount roughly the same as the length of the second part below the upper edge of the first part 10.

Figure 5:
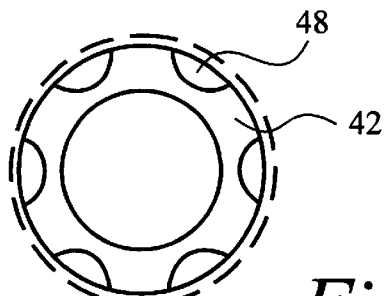
FIG. 5 is an end view of FIG. 4.

FIGS. 4–5 illustrate a second part 30' which is similar in size and shape to the second part 30 of FIG. 2. However, second part 30' includes a plurality of flutes 48 where a tool (not shown) can engage and rotate the second part 30' into the first part 10 as the threaded stem 32' is screwed into a threaded bore of an implant. When the two parts 10 and 30' are assembled, as shown in FIG. 4, the locking tapers 22 and 38' engage to frictionally lock the two parts 10 and 30' against relative rotation. With the stem 32' screwed into an implant and the socket 12 non-rotationally engaged on the implant, the two-piece abutment of the invention is non-rotationally fixed to the implant.

Figure 3:
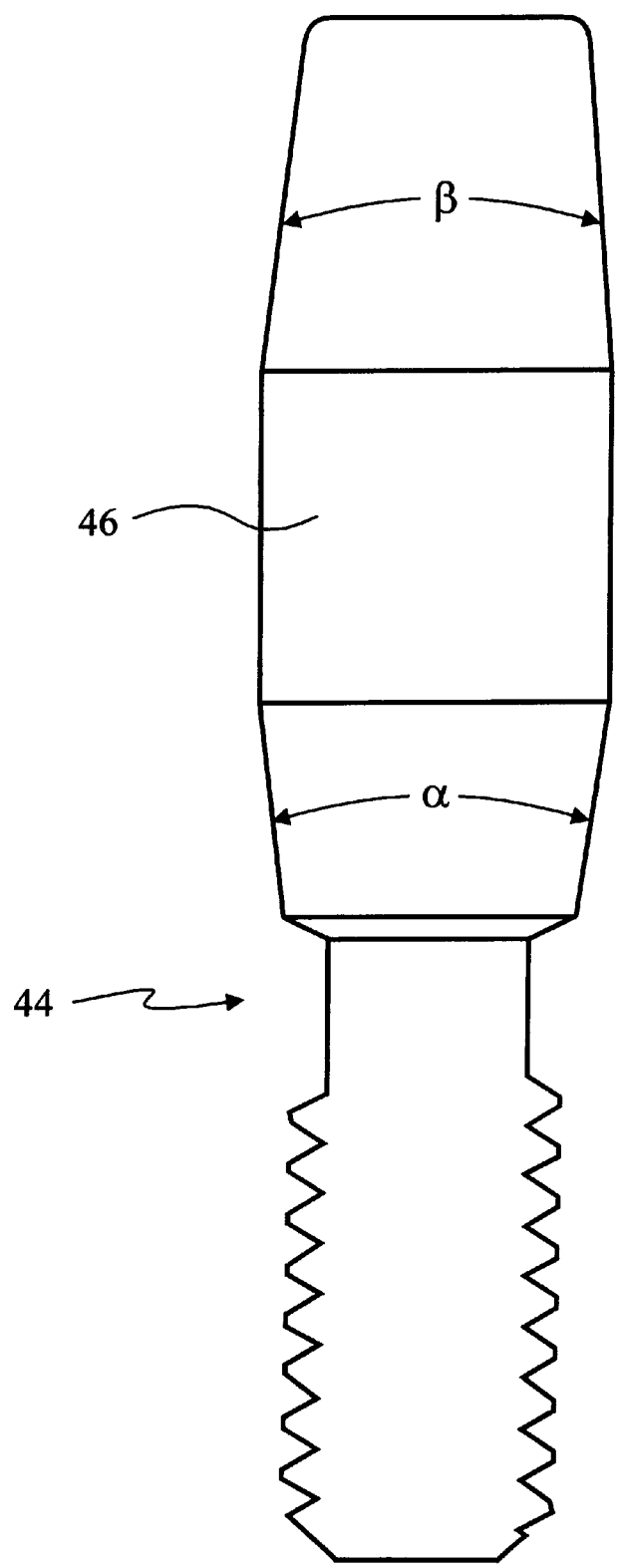
FIG. 3 is a side view of an alternative second part having a longer post.
Figure 6:
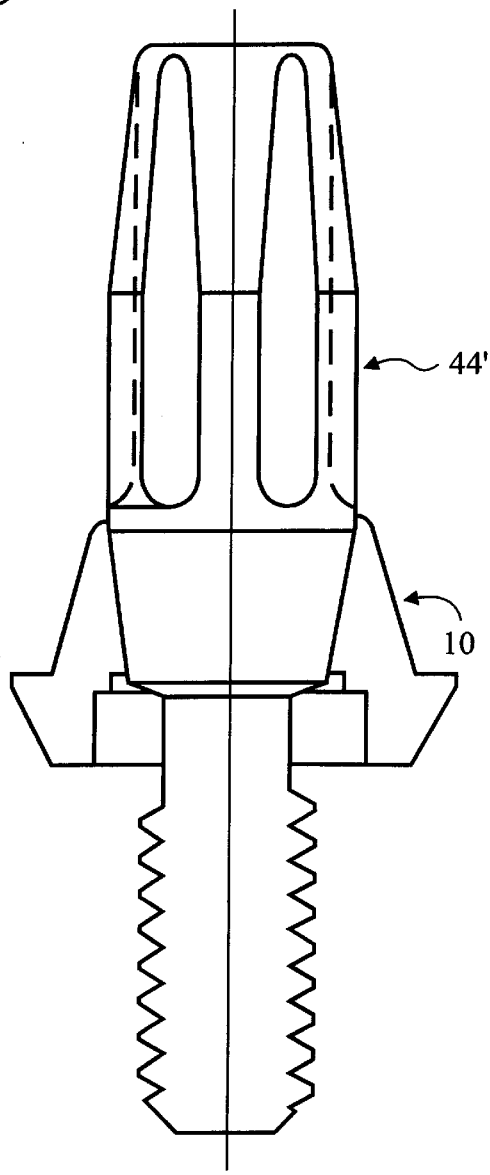
FIG. 6 is a side view of an assembly having a longer second part with flutes and the first part of FIG. 1.

FIG. 6 shows a longer second part 44' that is similar to the second part 44 which has a larger post and engages the first part 10 (FIG. 3). The male locking tapers of both second parts 44' and 30' (FIG. 4) are interchangeably the same such that both second parts 44' and 30' may be used with the same first part 10. Similarly, first parts of different external configurations may be provided as is evident in FIGS. 7 and 10 below. It will be understood that the interchangeability of components in this invention lends itself to providing components in sets that may be adapted to various dental restoration tasks depending on the needs of a particular patient. Once the two parts 10 and 30 are in their final position on the implant, the clinician can then prepare the post 34 such that it conforms to the precise height and angle of the adjacent teeth. The clinician performs this task by cutting into the surface of the post 34. In essence, the two-piece abutment system can be used in its manufactured configuration or adjusted to a unique configuration that is suited for a particular patient.

FIGS. 7A–7C illustrate an alternative first part 60 which has a body 61 with a substantially cylindrical outer surface 62. A bore 64 extends through the body 61 and includes a socket region 66. The socket region 66 is polygonal (hexagonal in this case) and includes an anti-rotational structure 68 in each of its six corners 70. These anti-rotational structures 68 are discussed in detail below with reference to FIGS. 16a–16f.

The bore 64 also includes a locking taper region 72 and an intermediate region 74. The locking taper region 72 engages a correspondingly shaped male taper on a post of a second part of the two-piece abutment like second parts shown in FIGS. 8–9. The angle of the taper is typically the same as the range given for angle α in FIG. 1. Moreover, the style of the first part 10 in FIGS. 1–6 and the style of the first part 60 in FIGS. 7A–7C may be in the same dental kit such that the clinician chooses the style that is best suited for his or her patient. Preferably, the internal taper angle is the same for the first parts 10 and 60 so that same type of second part can be utilized. Additionally, a dental set may include not only different styles, but it may include different sizes of each style.

The first part 60 includes a bottom surface 76 which is adjacent the socket region 66 and engages the implant. At the other end of the first part 60, a shoulder 78 resides which provides for a surface against which another component may abut. An externally tapered region 80 is at the extremity of the first part 60.

FIGS. 8A and 8B illustrate a second part 90 that is compatible with the first part 60 in FIGS. 7A–7C. The second part 90 includes a threaded shaft 92 which mates with an internally threaded bore of the implant. A male tapered portion 94 is adjacent the threaded shaft 92 and matches the locking taper region 74 of the first part 60. An intermediate portion 95 is adjacent the tapered portion 94 and is generally cylindrical. Lastly, an upper portion 96 that reduces in cross section is located at the extremity of the second part 90. As is seen only in FIG. 8B, the upper portion 96 has a flattened surface 98 which provides for a surface to grip when rotating the second part 90. The flattened surface 98 also provides for the non-rotational mating with another component encompassing upper portion 96 assuming that component includes a flat interior surface that engages the flattened surface 98.

FIGS. 9A–9B illustrate an alternative second part 100 which differs from the second part 90 in FIGS. 8A–8B only in that it contains a threaded bore 101 in its upper portion 106. The threaded bore 101 is used to attach other components to the second part 100 as will be shown in FIGS.

12–15. Thus, the threaded shaft 102, the male tapered portion 104, the intermediate portion 105, and the flattened surface 108 on the upper portion 106 are the same structures that are present on the second part 90 in FIGS. 8A–8B.

Figure 10A:
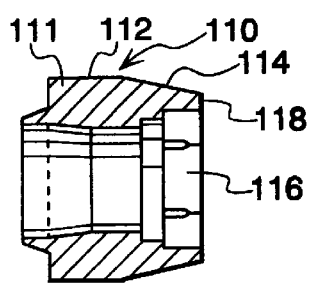
FIGS. 10A–10C illustrate alternative first parts in which the exterior surface is non-round.
Figure 10B:
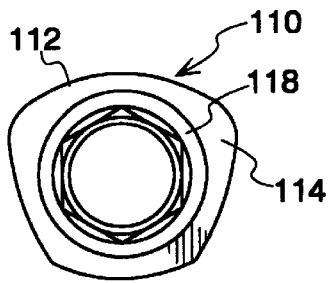
Figure 10C:
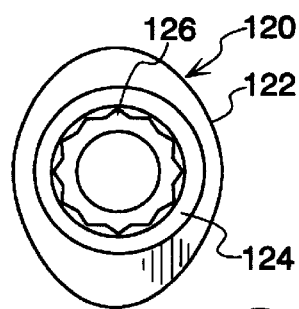

FIGS. 10A–10C illustrate yet other alternative first parts. FIGS. 10A and 10B illustrate a non-round shape to a first part 110. The body 111 has an outer surface 112 that is non-round initially but then gradually changes to round in a tapered section 114 adjacent the socket 116. Thus, the bottom surface 118 is round to mate with a cylindrical implant. By utilizing a non-round shape, the gingiva above the implant can be formed and maintained in the shape that natural tooth had in that region. Consequently, a more aesthetically pleasing prosthesis can be developed since it will emerge from the gingiva in the same contour as the natural tooth did.

FIG. 10C illustrates a first part 120 which deviates from the first part 110 of FIGS. 10A–10B in two ways. First, an oval shape is present on an exterior surface 122 of the first part 120. This oval shape also gradually changes to a round shape at the lower surface 124 so as to mate with a cylindrical implant. And, a socket 126 is present that includes the shape of a twelve-pointed star that allows the first part 120 to be mounted on the hexagonal boss of an implant in twelve orientations. It should be noted that the internal structure of the first parts 110 and 120 of FIGS. 10A–10C is the same as the previously described first parts so as to be interchangeable those devices. Expanding the dental kit to include non-round shapes offers more options to the clinician and allows him or her to select a first part that is best suited for the patient.

Figure 11A:
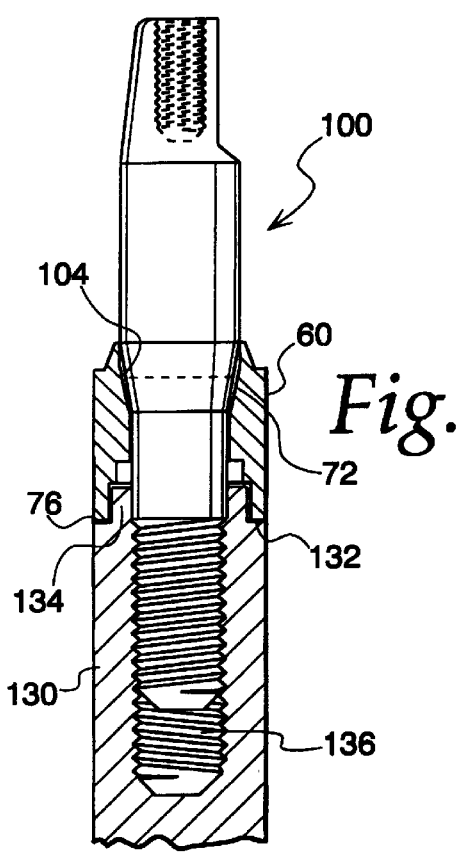
FIGS. 11A–11B illustrate the assembly of the first part of FIG. 7 and the second part of FIG. 9 mounted on an implant.
Figure 11B:
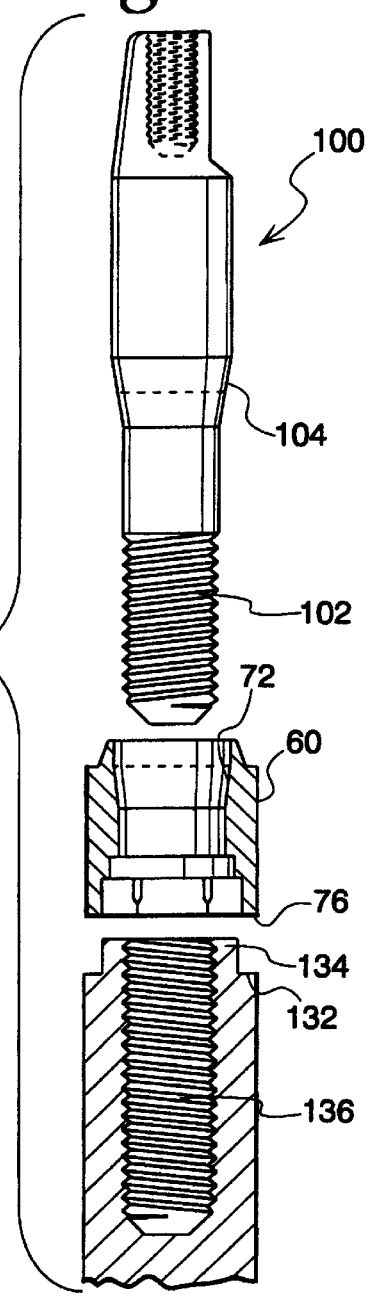

FIGS. 11A–11B illustrate the first part 60 of FIG. 7 and the second part 100 of FIG. 9 mounted on an implant 130. The implant 130 has an upper table 132 on which the lower surface 76 of the first part 60 mates. The socket 66 of the first part 60 captures the correspondingly shaped boss 134 on the implant 130. As the threaded shaft 102 of the second part 100 is screwed into a threaded bore 136 in the implant 130, the locking tapered surfaces 104 and 72 engage and tighten. Typically, the torque required to complete the assembly of the first and second parts 60 and 100 on the implant 120 is in the range from about 30 N·cm to about 40 N·cm. Once assembled, the two-piece abutment serves numerous functions as is described below.

Figures 12, 13:
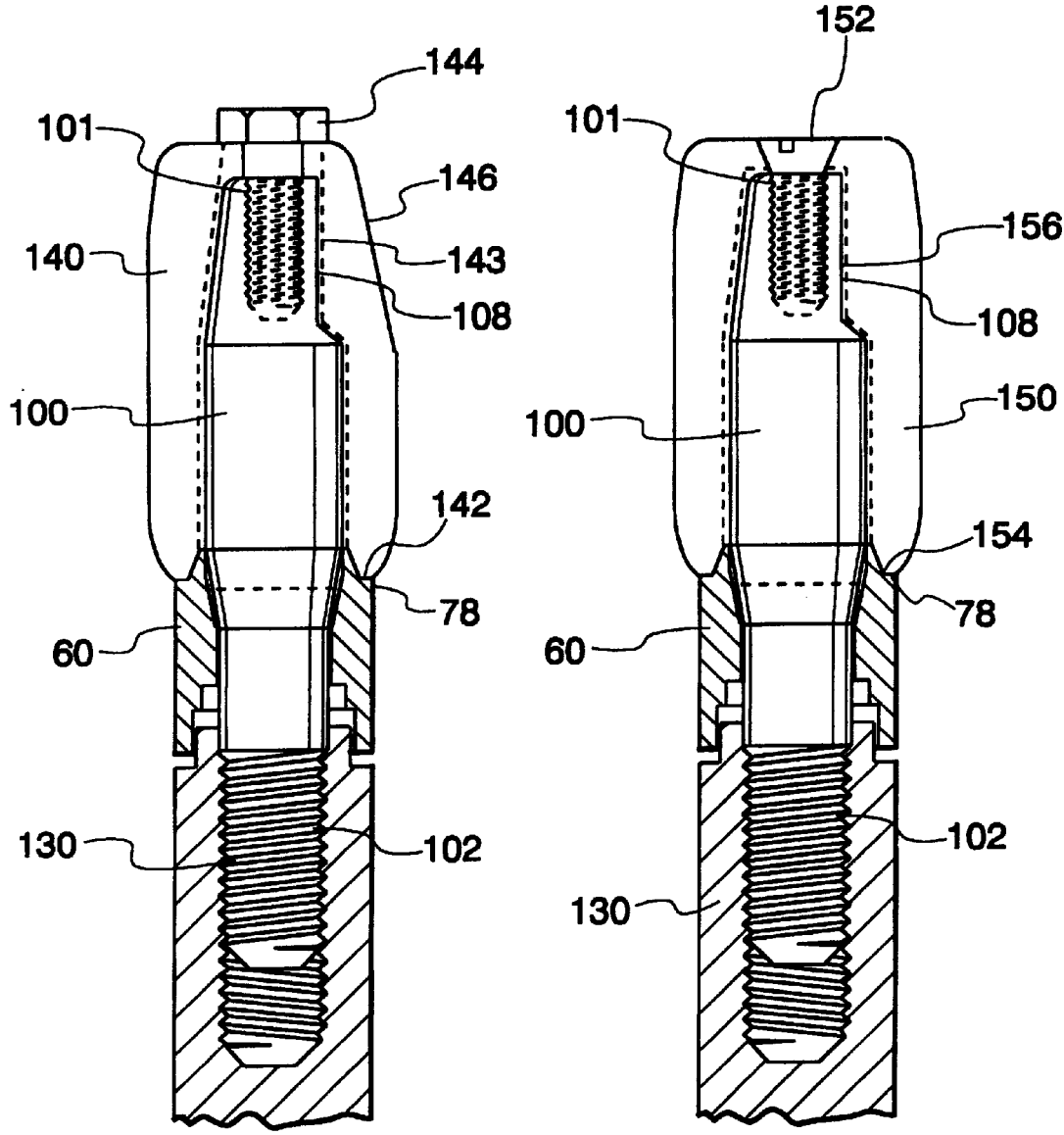
FIG. 12 illustrates the assembly of FIG. 11 with an impression coping attached to the post.
FIG. 13 illustrates the assembly of FIG. 11 with a healing cap attached to the post.

FIG. 12 illustrates an impression coping 140 fixed on the second part 100. The impression coping 140 has a bottom surface 142 which engages the shoulder 78 of the first part 60. The interior surface of the impression coping 140 has a contour that matches the contour of the exterior surface of the second part 100. Thus, the interior surface has a flat region 143 to match the external flattened surface 108 of the second part 100 to resist rotation therearound. The impression coping 140 also includes a wide-head screw 144 which threadably engages threaded bore 101 and holds the impression coping 140 on the second part 100. The impression coping 140 includes an external flat side 146 which allows for the impression coping 140 to be properly realigned within the impression material after the impression is made. Instead of one flat side 146, the coping 140 can have several surfaces for non-rotationally engaging the impression material. As shown, the impression coping 140 is a transfer coping in that after the impression is taken, the impression material is removed without the coping 140 be carried with it. The screw 144 is removed and coping 140 is "transferred" back into the impression material with the flat surface 146 being aligned with the flat surface within the cavity of the impression material. The coping 140 is then mounted on an analog of the implant 130 and the first and second parts 60 and 10 and a model of the region is made.

Alternatively, the screw 144 could be elongated with a head that extends above the impression material. After the impression material has been placed at the site, the elongated screw, which is exposed through the impression material, is unscrewed. The coping 140 would then be retained within, or "picked-up" by, the impression material when it is removed from the site. Thus, the impression coping 140 could also be used as a pick-up type impression coping.

Furthermore, the second part 100 with its flat surface 108 could itself be used as an impression coping. That is to say that the impression material can be placed directly over the second part 100. Then, after the impression material is removed, an angular registering mark is placed between the first part 60 and the second part 100 to ensure that they are realigned exactly on an implant analog when making the model to develop a permanent dentition. While the first and second parts 60 and 100 are removed, a temporary abutment could be placed on the implant. Alternatively, a second set of the first and second parts 60 and 100 having a healing cap (FIG. 13) or a temporary dentition (FIG. 15) could be placed on the implant until the original set is returned with a permanent dentition attached.

FIG. 13 illustrates a healing cap 150 that is placed over the second part 100. The healing cap 150 is held on the second part 100 by a screw 152 that threadably engages the threaded hole 101. The screw 152 is approximately flush with the upper surface of the healing cap 150. The healing cap 150 has a lower surface 154 which engages the shoulder 78 of the first part 60. The interior surface of the healing cap 150 includes a flat portion 156 that engages the flattened side 108 of the second part 100 to resist rotation of the healing cap 150 around the second part 100.

Figure 14:
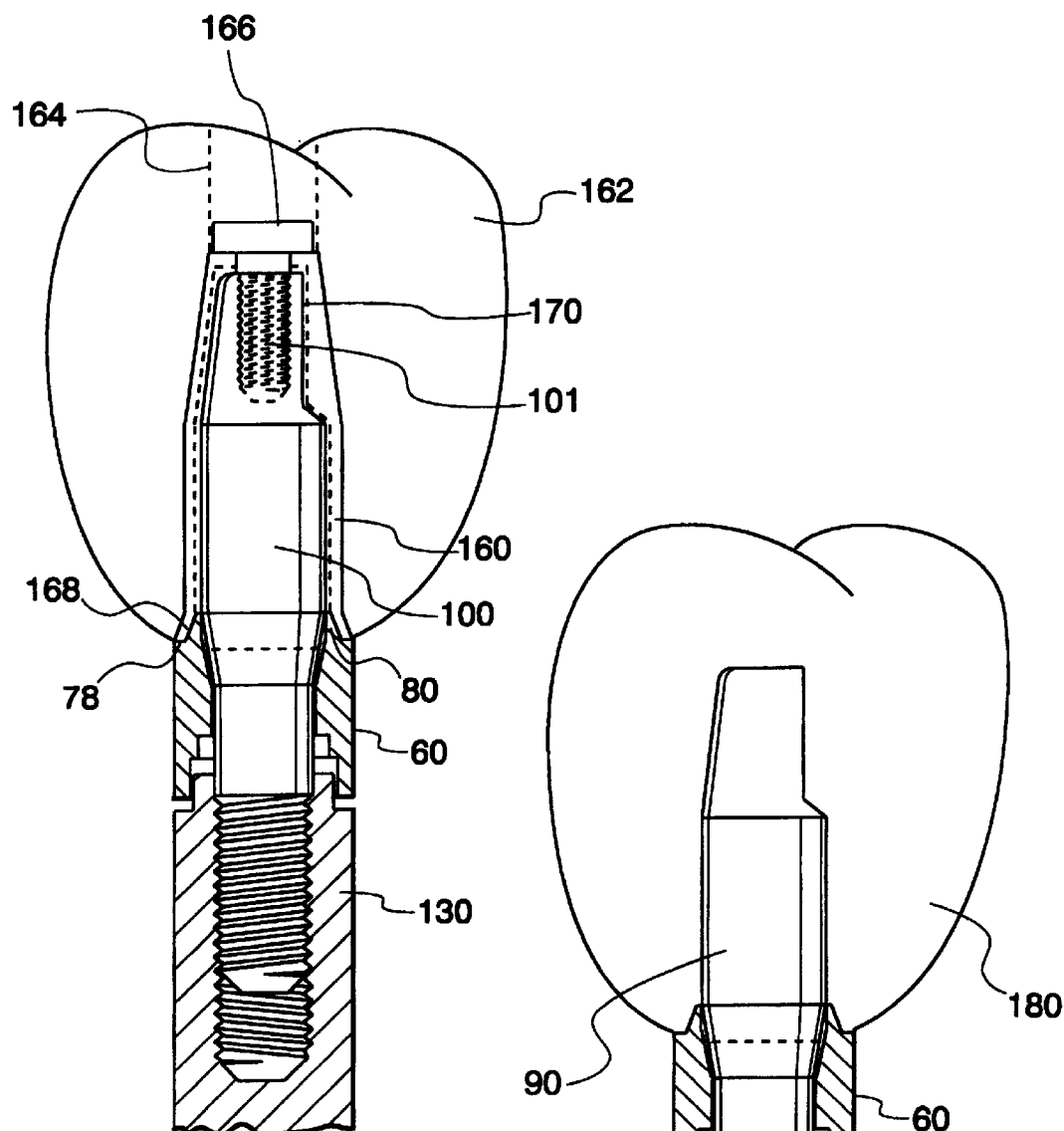
FIG. 14 illustrates the assembly of FIG. 11 with a prosthetic tooth mounted on a gold cylinder that is attached to the post.

FIG. 14 illustrates a cylinder 160 on which a prosthetic tooth 162 is permanently mounted. The prosthetic tooth 162 has a hole 164 at its upper end allowing a screw 166 to pass therethrough and connect the cylinder 160 to the second part 100 via the threaded bore 101. The cylinder 160 has a lower surface 168 which abuts the shoulder 78 of the first part 60. The interior surface of the cylinder 160 has a flat surface 170 that engages the flattened surface 108 of the second part 100. Thus, the cylinder 160 cannot rotate on the second part 100. Alternatively, the lower region of the cylinder 160 adjacent to the lower surface 168 could have a series of flats that could mate with a series of flats on the externally tapered region 80 of the first part 60 for resisting rotation.

Figure 15:
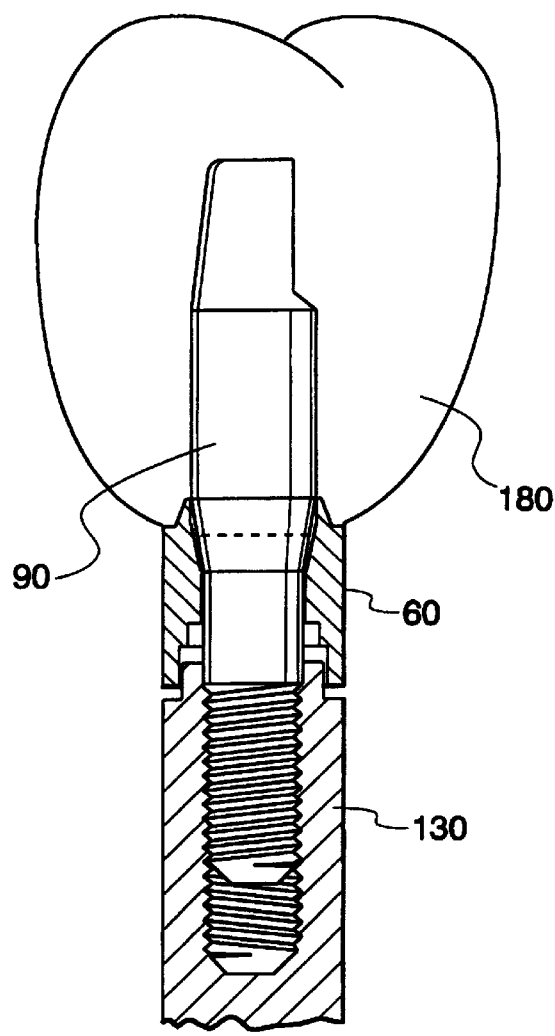
FIG. 15 illustrates a two-piece assembly with a prosthetic tooth directly attached to the post.

FIG. 15 illustrates the second part 90 of FIGS. 8A–8B mounted on the first part 60. The surface of the second part 90 has been prepared to receive cement and connect the second part 90 to an artificial tooth 180. The artificial tooth 180 may be made of an acrylic such that the clinician can modify it to fit precisely in the patient's mouth. The artificial tooth 180 can be a permanent tooth, or it may be attached to the second part 90 via a temporary cement such that it is a temporary dentition.

Figure 16A:
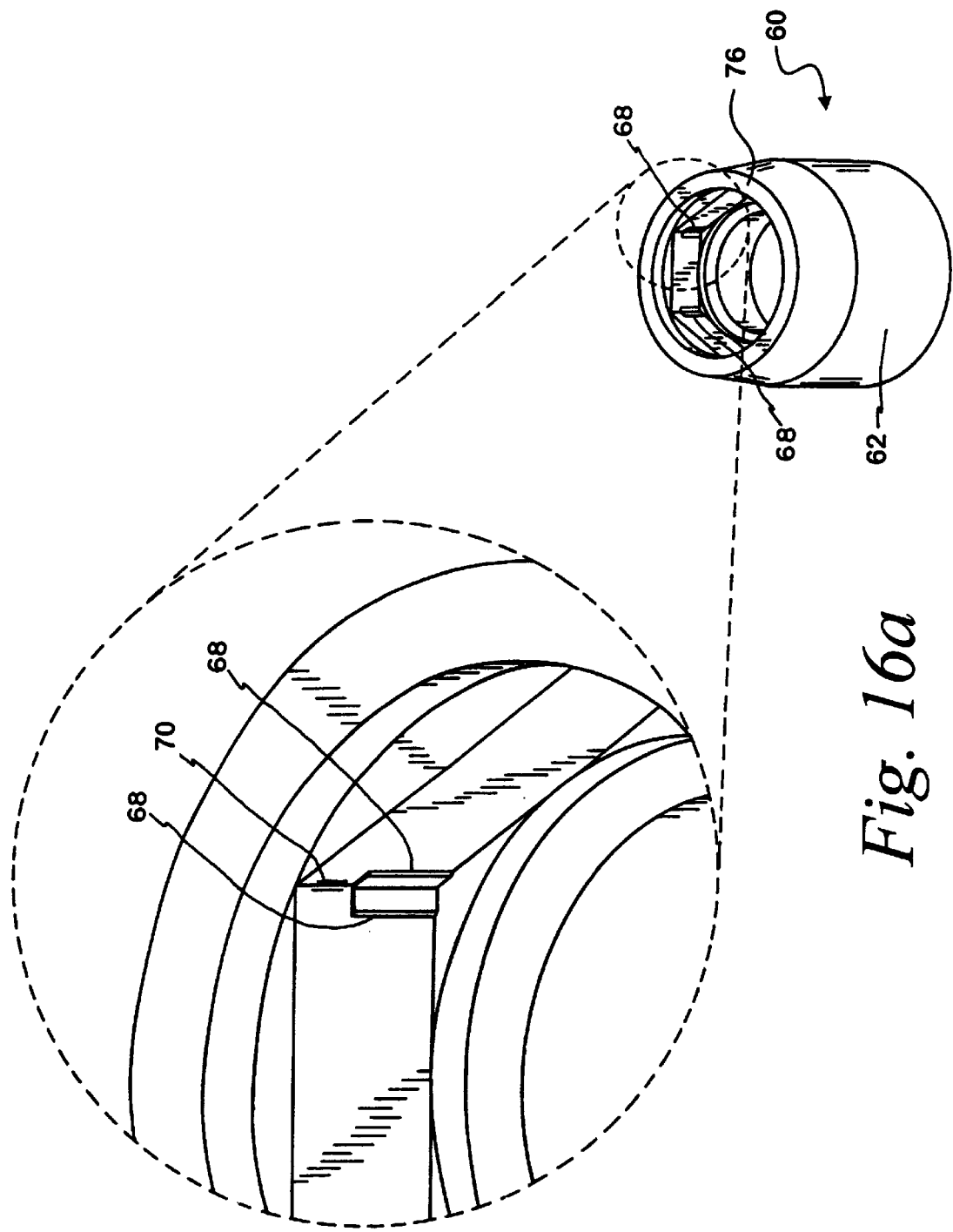
FIGS. 16a–16f illustrate the first part of the two-piece abutment having anti-rotational connecting structures in the socket region.

FIG. 16a is a detailed view of the first part 60 showing the corners 70 and the anti-rotational structures 68 placed thereon. Because of the tolerances in the boss of the implant and the socket, these two-pieces never fit tightly within each other. Therefore, there is always a slight rotation between the parts. Typically, when a screw holds down an abutment, the torque is used to produce tension in the screw as its threads engage the implant. In the present invention, the torque on the second part is resisted by the friction at the engaged locking tapers of the first and second parts and by the tension produced by the engaging threads. Thus, the tension in the second part is typically less (because of the friction at the locking tapers that the torque overcomes) which increases the likelihood that the first part may loosen on the implant. One option is to decrease the cross-sectional area of the second part at a neck which increases the stress and increases the strain to hold the pieces tightly together. The second part 30 in FIG. 2 has such a neck between the threaded stem 32 and the male locking taper 38.

Figure 16E:
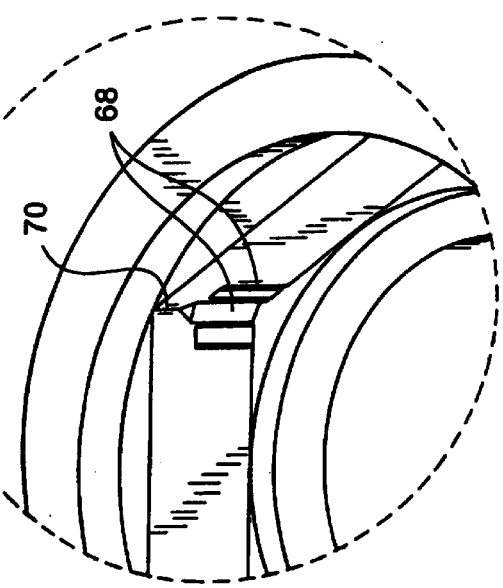

Alternatively, anti-rotational structures 68 can be used that make contact with sidewalls of the hexagonal boss of the implant at its corners to prevent rotation of the implant in the socket 66. These anti-rotational structures 68, as shown in FIG. 16*a*, are essentially shims located at the corners 70. Alternatively, the anti-rotational structures 68 can be removed somewhat from the corners 70, as is shown in FIG. 16*b*. Thus, they do not have to be located directly in the corners 70.

Figure 16C:
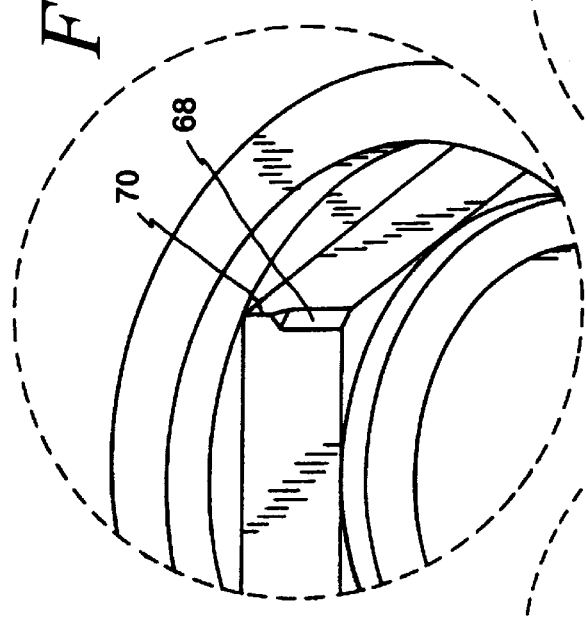

FIG. 16*c* illustrates the anti-rotational structures 68 being a corner block as opposed to being shims. The corner blocks come into firm contact with the hexagonal boss of the implant at the corners of the implants. The corner blocks are dimensioned so that opposite pairs of the blocks will squeeze the hexagonal boss between them to hold the first part 60 tightly on the implant.

Figure 16D:
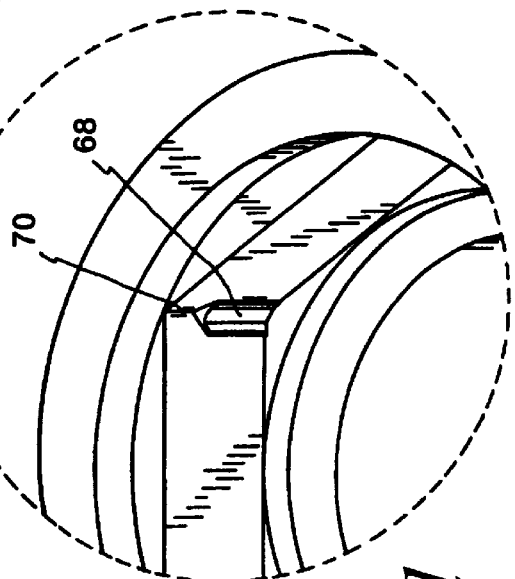
Figure 16B:
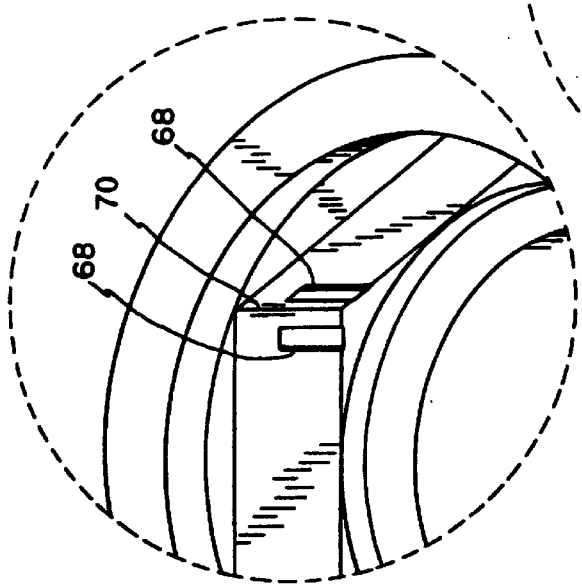

FIG. 16*d* shows anti-rotational structures 68 at the corners 70 which have the squeezing effect from the corner blocks as described above with reference to FIG. 16*c*. Additionally, the anti-rotational structures 68 have a shim-type structure which enhances the contact of anti-rotational structures 68 with the sides of the boss of the implant.

FIG. 16*e* shows an anti-rotational structure 68 in still another embodiment. Here, a corner block is in the corner 70 and shims are positioned outside the corner.

Figure 16F:
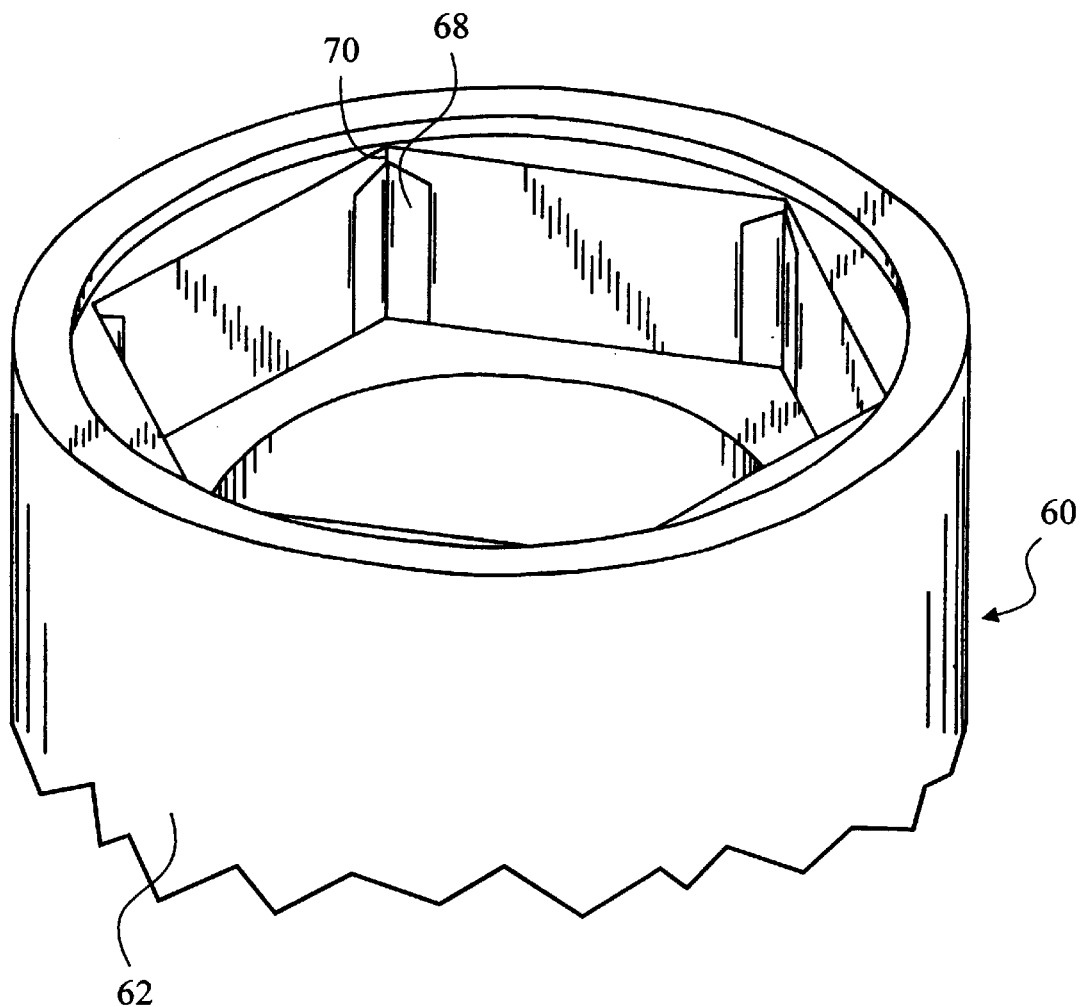

FIG. 16*f* shows a preferred embodiment of the invention which includes modified anti-rotational structures 68 to facilitate a smooth entrance of the hexagonal boss into the socket while still providing an anti-rotational effect. The improvement can best be observed by comparing the anti-rotational structures shown in FIG. 16*f* to those shown in FIG. 16*a*. Referring to FIG. 16*a*, it is noted that the corner anti-rotational structures 68 have upper edges which are substantially parallel to and spaced below the upper edge of the socket. Upon initial insertion and until encountering the upper edge of the corner anti-rotational structures 68, the hexagonal boss fits within the socket with the same degree of rotational looseness as encountered in the prior art. As the boss of the implant is inserted further into the socket, it encounters an abrupt "tightening" of fit along the upper edge of the corner anti-rotational structures 68. The embodiment shown in FIG. 16*f* facilitates entry of the boss into the socket by angling the upper edges of each corner shim pair relative to the upper edge of the socket. Specifically, the top edges of each shim pair are angled toward each other and toward the upper edge of the socket so that they meet at an apex near the upper end of a corner of the socket. As the boss is inserted into the socket, it initially encounters the same degree of rotational looseness as in the prior art, but quickly reaches the apexes of the angled shim pairs. As the boss of the implant penetrates further into the socket, the sidewalls of the boss contact the ends of the angled upper edges of the anti-rotational structures nearest the corners of the socket. Then, as the boss is further inserted into the socket, the sidewalls gradually come into contact with progressively increasing surface areas of the anti-rotational structures until the anti-rotational structures are in full contact with the boss and achieve the full anti-rotational effect. It may be noted that while the improvement of FIG. 16*f* has been described in relation to FIG. 16*a*, the same type of improvement may be achieved by angling the upper edges of the anti-rotational structures 68 in other embodiments such as those shown in FIGS. 16*b*, 16*d*, and 16*e*.

FIGS. 17–20 illustrate various alternative embodiments of the first part of a two-piece abutment which is made primarily of ceramic. Unlike the previous permanent abutments which have been described, the abutments in FIGS. 17–20 are more aesthetically pleasing since the ceramic material is a lighter color which is not readily seen through the gingival tissue.

Figure 17:
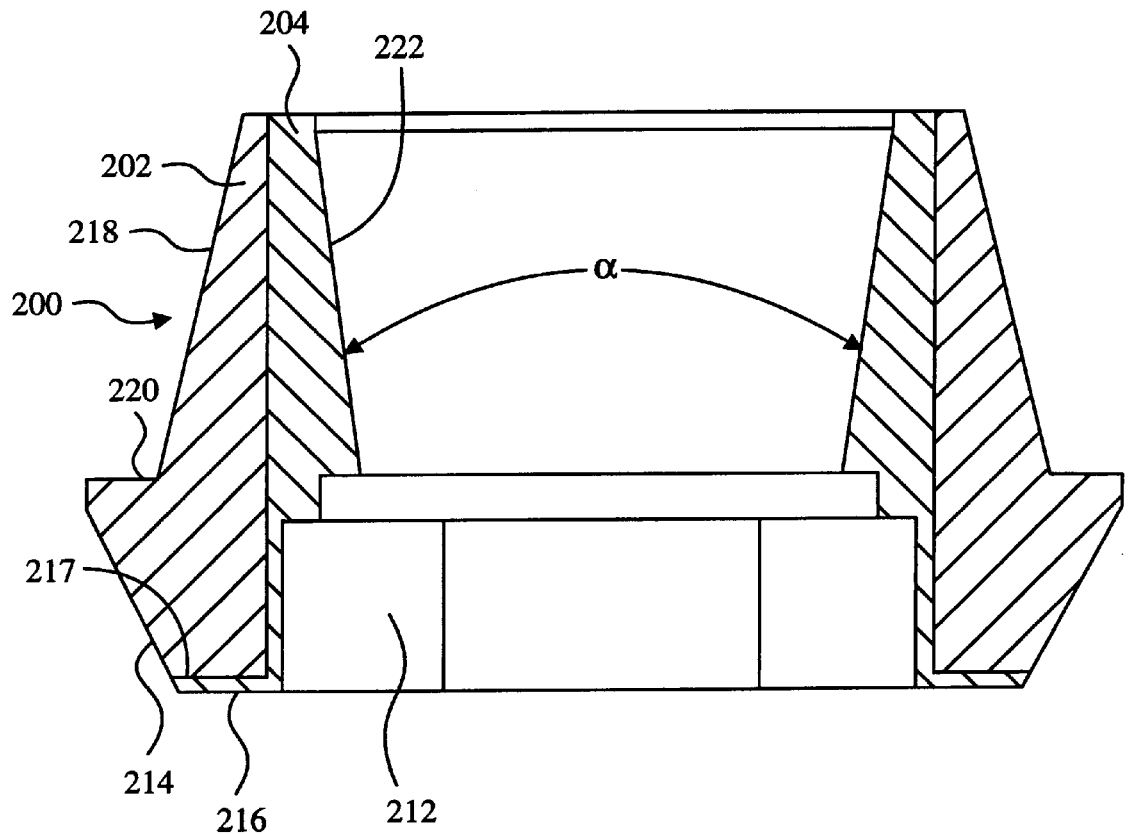
FIG. 17 illustrates a longitudinal cross-section of the tubular first part of a two-piece abutment which is made primarily of a ceramic material.

In FIG. 17, a ceramic abutment 200 includes a ceramic outer piece 202 surrounding a metallic core 204. The metallic core 204 include a socket 212 which engages the hexagonal boss of an implant. The metallic core 204 also has a lower surface 216 for engaging the annularly-shaped surface which surrounds the hexagonal boss on the top of the implant. The ceramic outer piece 202 includes a lower section 214 which tapers upwardly away from the lower end 216 and terminates at a shoulder 220. Above the shoulder 220 is an upper section 218 of the ceramic outer piece 202 which decreases in cross-section as it proceeds away from the shoulder 220 toward the uppermost end of the ceramic abutment 200.

The lower surface 217 of the ceramic outer piece 202 preferably engages the upper surface of the lower end 216 of the metallic core 204. Consequently, the upper surface of the implant only engages the metallic core 204 and does not engage the ceramic outer piece 202. This ensures that the ceramic outer piece 202, which is usually a harder material than the titanium implant, does not mar the implant. In one preferred embodiment, the metallic core 204 is made of titanium while the ceramic outer piece 202 is made of aluminum oxide. In addition to aluminum oxide, the ceramic outer piece 202 can also be made of zirconium.

Like the previous embodiments of FIGS. 1–16, the metallic core 204 includes a locking taper 222 for engaging a corresponding taper on a post, such as the post 30 in FIG. 2. Thus, the resulting assembly looks no different than the assemblies shown in FIGS. 4 and 6, except that the outer portion of the first part would be of a light colored ceramic (e.g. aluminum oxide).

Because the post 30 is usually made of a metal (e.g. titanium), it is preferable for the locking taper 222 to also be made of metal. If the locking taper is made of a hard ceramic, then the engagement of the ceramic locking taper and the post may result in a high coefficient of friction. Higher insertion torques would then be needed to result in the same amount of tension in the post (i.e. the force holding the ceramic abutment 200 on the implant) which is brought about through the threaded engagement of the lower stem of the post and the internal bore of the implant. Additionally, the hardness of the ceramic locking taper may cause it to mar the surface of the titanium post. However, it is possible to provide a biocompatible lubricant to reduce friction if a ceramic metal is used.

While FIG. 17 illustrates the metallic core extending to the uppermost end of the abutment 200, it may extend to a point where the tapered surface is below the uppermost end. However, enough material should be present to perform the locking function with the post.

In one embodiment, the metallic core 204 is pressfit into the ceramic outer piece 202. One way to achieve this pressfit engagement is by cooling the metallic core 204 such that it decreases in cross-sectional size due to its coefficient thermal expansion and allowing it to heat up to room temperature whereby it expands into a tight engagement with the ceramic outer piece 202. Additionally, the metallic core 204 can be attached to the ceramic outer piece 202 through an adhesive.

Figure 18:
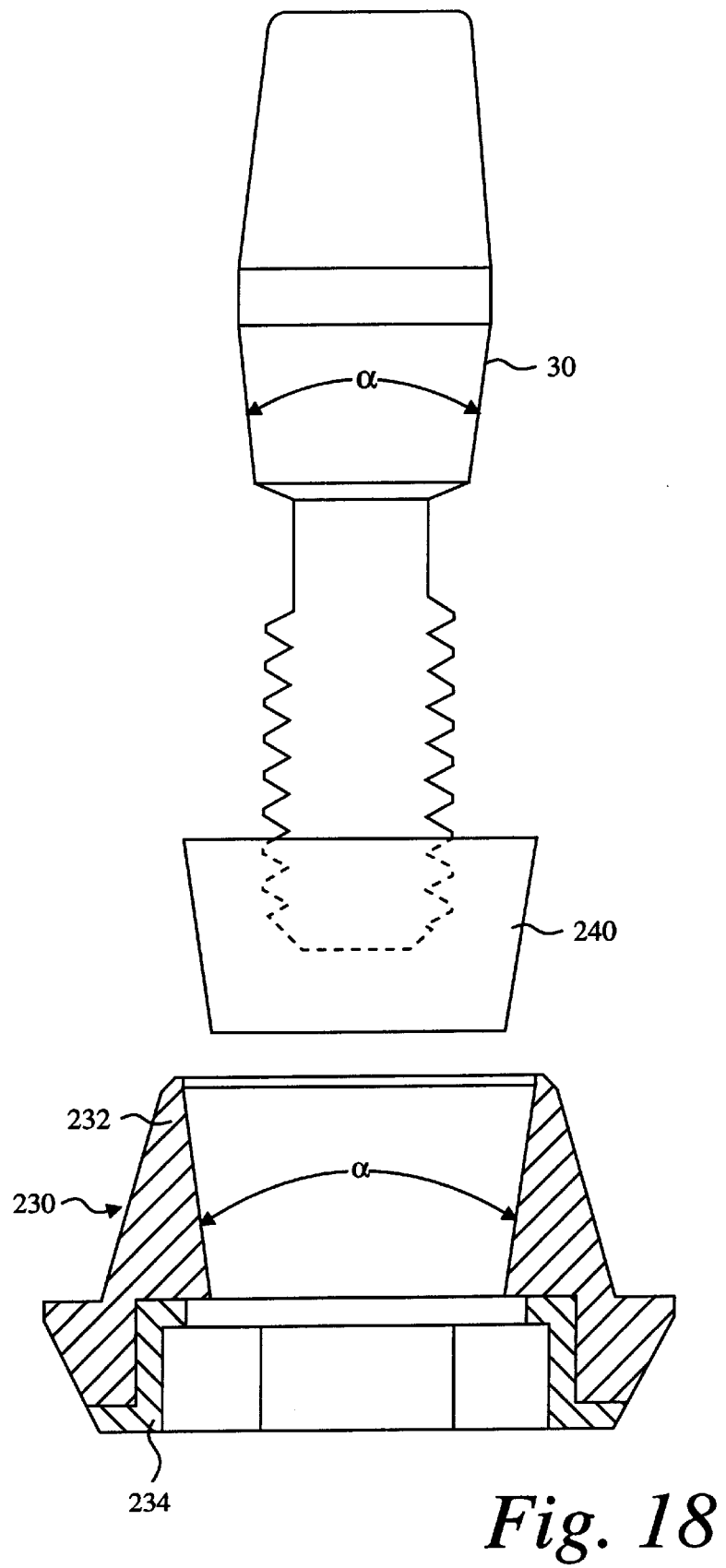
FIG. 18 illustrates a longitudinal cross-section of an alternative first part of a two-piece abutment which is made primarily of a ceramic material.

FIG. 18 illustrates an alternative ceramic abutment 230 which includes a ceramic outer piece 232 and a metallic core 234. Instead of the metallic core 234 extending entirely to the uppermost surface of the ceramic abutment 230, the metallic core 234 is only placed inside the ceramic outer piece 202 at its lower end to form a non-round (e.g. hexagonal) socket. Because it is preferable to have the tapering section of the post 30 engage a metallic surface, instead of a ceramic surface, a metallic foil 240 is placed into the ceramic outer piece 202 prior to insertion of the post. The foil 240 has a frusto-conical shape such that fits within the tapered aperture of the ceramic outer piece 232. Thus, as the post 30 is threaded into the ceramic abutment 230, the tapering section of the post engages the metallic foil 240 which reduces the torque required to overcome the frictional engagement at the locking taper surface. The foil 240 can be made of gold or a gold alloy.

Figure 19:
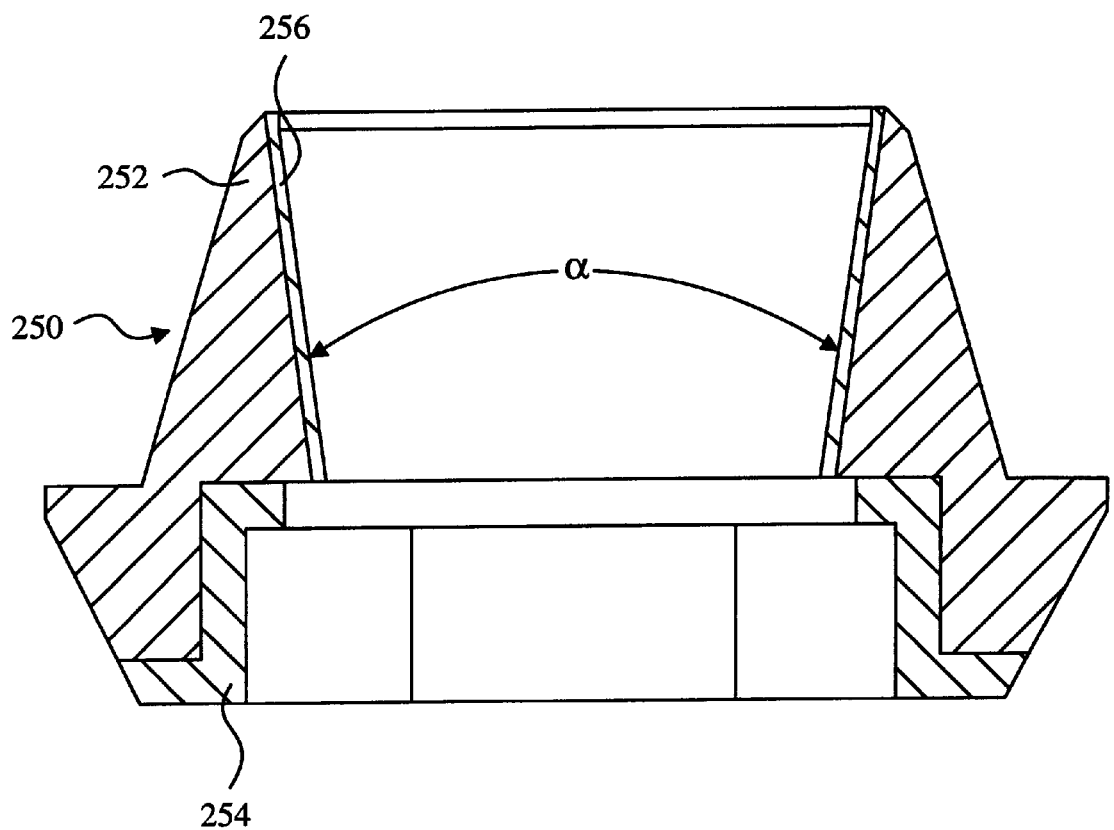
FIG. 19 illustrates yet a further alternative of a first part of a two-piece abutment which is made primarily of a ceramic material.

FIG. 19 is very similar to FIG. 18 in that a ceramic abutment 250 includes a ceramic outer piece 252 and a lower metallic core 254. Additionally, the ceramic abutment 250 in FIG. 19 includes an upper metallic core 256 which fits into the ceramic outer piece 252 thereby forming a metallic tapering surface for the ceramic abutment 250 which engages a corresponding tapering section of the post. In comparison with FIG. 17 which has a unitary metallic core 204, FIG. 19 has two metallic metallic cores for accomplishing the same purpose. By separating the metallic core into two pieces, varied internal configurations are available for the ceramic outer piece 232 since the two metallic pieces 254 and 256 can be inserted from both ends. This is different than the configuration of FIG. 17 where the ceramic portion has a smooth, continuous opening to receive the smooth continuous external surface of the metallic core. The lower metallic core 254 and upper metallic core 256 can again be pressfit into engagement with the ceramic outer piece 252 or attached thereto the end via an adhesive.

Figure 20:
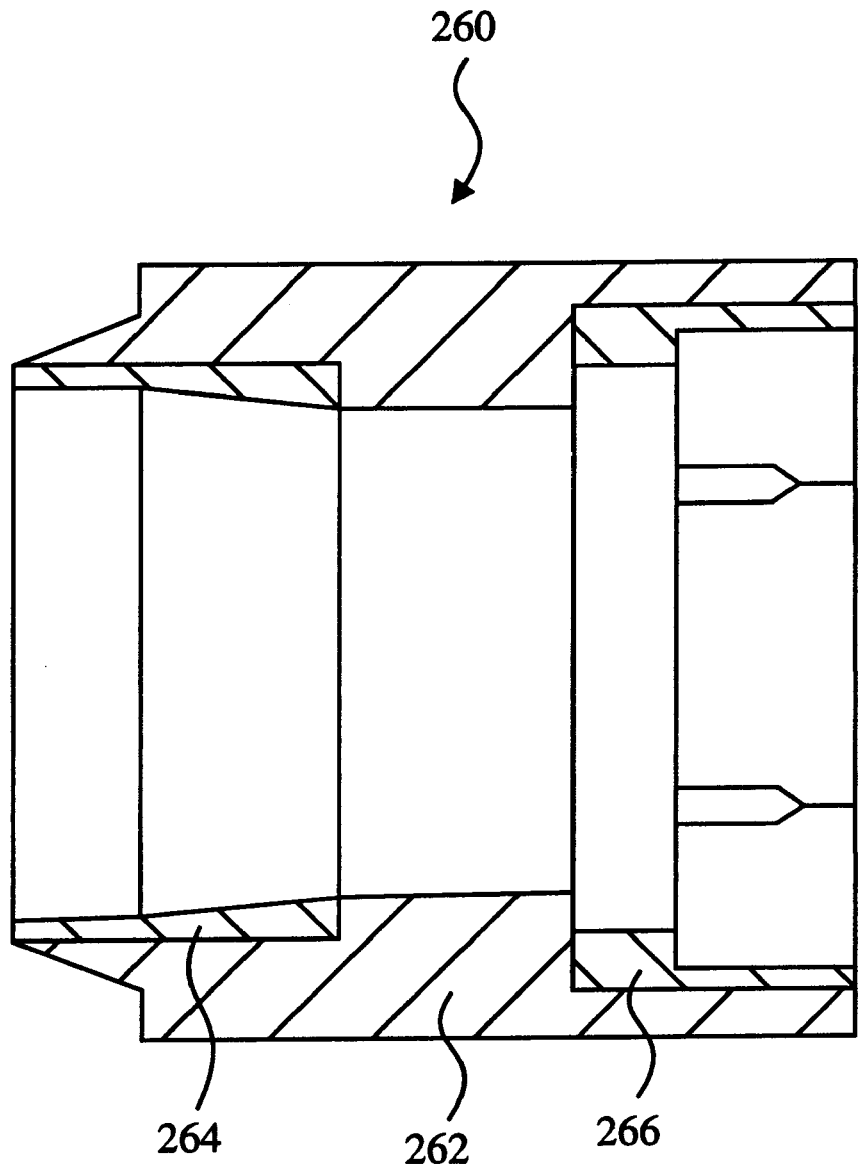
FIG. 20 illustrates yet another alternative first part of a two-piece abutment which is made primarily of a ceramic material.

Another ceramic abutment 260 is illustrated in FIG. 20 which is very similar to the abutment shown in FIG. 7. The ceramic abutment 260 includes a ceramic outer piece 262 and upper and lower metallic cores 264 and 266. Thus, the metallic cores 264 and 266 are very similar to the metallic cores described in FIG. 19. The primary difference between the ceramic abutment 260 in FIG. 20 and the ceramic abutment 250 in FIG. 19 is that the ceramic abutment 260 has a different exterior configuration brought about through the configuration of the ceramic outer piece 262. While the ceramic outer piece 262 has a circular cross-sectional configuration, the ceramic outer piece 262 could also be manufactured to have a non-round cross-section such that it would closely match the contour of a natural tooth as it emerged through the gum tissue, as shown by the abutments in FIGS. 10a–10c.

While the ceramic abutments shown in FIGS. 17–20 having been described as being produced through the mechanical attachment of a metallic core to a ceramic outer piece, other possibilities exist for resulting in the same configuration. For example, the ceramic material (e.g. aluminum oxide) can be grown onto the metallic core. One such process entails having the ceramic vaporized and deposited onto the metallic core through a process known as physical vapor synthesis. Such a process is described in the article entitled "Creating Nanophase Materials," by Siegel in *Scientific American*, December 1996, Vol. 275, No. 6, pp. 74–79, which is herein incorporated by reference in its entirety. The result of such a process is a very durable ceramic formed on the metallic core.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention.

What is claimed is:

1. An abutment for supporting a dental prosthesis, said abutment being attached to a dental implant that is integrated with living jawbone, said dental implant including a threaded bore and a boss protruding away from an upper portion thereof, said abutment comprising:

a first part constructed of a metallic core and a ceramic outer piece positioned around said metallic core and attached thereto, said first part including a bore extending therethrough along a central axis and a socket for receiving said boss of said implant, a portion of said bore being defined by a tapered surface that tapers inwardly at a predetermined angle with respect to said central axis in a direction toward said socket, said first part including an annular surface for supporting said dental prosthesis, a portion of said first part above said annular surface decreasing in cross-section in the direction of an upper end of said first part; and a second part for extending through said bore of said first part, said second part including a threaded stem for engaging said threaded bore of said implant and a post protruding above said first part, said second part including an outer surface with a tapered portion that tapers at an angle substantially the same as said predetermined angle for engaging said tapered surface of said first part.

2. The abutment of claim 1, wherein said metallic core forms said socket and engages said boss of said implant.

3. The abutment of claim 2, wherein said metallic core further engages a top surface of said implant adjacent to said boss.

4. The abutment of claim 1, wherein said metallic core is a unitary piece that extends from a lowermost surface of said abutment to at least near an uppermost surface of said abutment.

5. The abutment of claim 4, wherein said metallic core forms at least a portion of said tapered surface.

6. The abutment of claim 5, wherein said metallic core forms said socket and engages said boss of said implant.

7. The abutment of claim 1, wherein said metallic core forms at least a portion of said tapered surface.

8. The abutment of claim 1, wherein said second part is metallic.

9. The abutment of claim 1, wherein said metallic core includes at least two separate metallic pieces.

10. The abutment of claim 9, wherein one of said two metallic pieces of said core forms said tapered surface and the other of said two metallic pieces of said core forms said socket.

11. The abutment of claim 1, wherein said post engages a wall defining said bore immediately adjacent to said upper end of said first part.

12. The abutment of claim 1, wherein said annular surface separates first and second regions of said first part, said said annular surface being on said ceramic outer piece, said first region being adjacent to said implant and flaring outwardly from said central axis in a direction away from a lower end, said second region flaring inwardly toward said central axis in a direction toward said upper end.

13. The abutment of claim 1, wherein said predetermined angle is in the range from about 5° to about 20° for providing a locking taper between said first and second parts.

14. The abutment of claim 1, wherein said post includes a threaded hole for receiving a screw to attach a component onto said second part.

15. The abutment of claim 1, wherein said socket and said boss have a non-round shape to resist the rotation of said abutment around said implant.

16. The abutment of claim 1, wherein said socket is a portion of said bore.

17. The abutment of claim 1, wherein said first part has an exterior surface for engaging soft tissue overlying said jawbone, said exterior surface having a portion that is non-round in cross-section.

18. The abutment of claim 1, wherein said post protrudes above said first part by a distance that is larger than the height of said first part.

19. The abutment of claim 1, further including a foil placed between said tapered surface of said first part and said tapered portion of said second part.

20. The abutment of claim 1, wherein said portion of said first part above said annular surface is separate from said annular surface.

21. The abutment of claim 1, wherein said annular surface is generally perpendicular to said central axis of said first part.

22. An abutment for attaching to a dental implant embedded in living jawbone and having an upper surface with a fitting, said abutment comprising:

a tubular first part with a metallic core and a ceramic outer portion surrounding said metallic core, said tubular first part having a bore extending therethrough along a central axis, said bore including a tapered portion, said first part including a shoulder for supporting a dental prosthesis positioned below an upper surface of said first part such that said dental prosthesis fits over at least a portion of said first part; and an elongated second part for extending through said bore of said first part, said second part including a threaded stem for engaging a threaded bore of said implant and a post protruding above said first part, said post portion for laterally supporting said dental prosthesis, said elongated second part including a tapered outer surface for engaging said tapered portion of said bore.

23. The abutment of claim 22, wherein said metallic core is a unitary piece that extends from a lower surface of said abutment to at least near said upper surface of said abutment.

24. The abutment of claim 23, wherein said metallic core forms said tapered surface.

25. The abutment of claim 22, wherein said metallic core includes at least two separate metallic pieces.

26. An abutment for attaching to a dental implant embedded in living jawbone and having an upper surface with a fitting, said abutment comprising:

a tubular first part with a metallic core and a ceramic outer portion surrounding said metallic core, said tubular first part having a bore extending therethrough along a central axis, said bore including a tapered portion tapering at an angle between about 5° and about 20°, said metallic core having a lower flanged portion for engaging said upper end of said implant; and an elongated part extending through said bore of said tubular first part and having a threaded stem for engaging a threaded bore of said implant and a post protruding above said first part, said elongated part including a tapered outer surface that tapers at said angle for forming a locking taper with said tubular first part.

27. The abutment of claim 26, wherein said metallic core includes at least two separate metallic pieces.

28. The abutment of claim 26, wherein said tapered portion of said bore is located on said metallic core.

29. The abutment of claim 28, wherein only said metallic core engages said implant.

30. The abutment of claim 29, wherein said tapered portion of said bore is located on said metallic core.

31. The abutment of claim 30, wherein said metallic core is a unitary piece.

32. The abutment of claim 26, wherein said metallic core is press-fit into said opening in said ceramic outer portion.

33. The abutment of claim 26, wherein said metallic core is attached to said ceramic outer portion with adhesive.

34. An abutment for supporting a dental prosthesis, said abutment being attached to a dental implant that is integrated with living jawbone, said dental implant including a threaded bore and a boss protruding away from an upper portion thereof, said abutment comprising:

a first part constructed of a metallic core and a ceramic outer piece positioned around said metallic core and attached thereto, said first part including a bore extending therethrough along a central axis and a socket for receiving said boss of said implant, a portion of said bore being defined by a tapered surface that tapers inwardly at a predetermined angle with respect to said central axis in a direction toward said socket, said metallic core includes at least two separate metallic pieces; and a second part for extending through said bore of said first part, said second part including a threaded stem for engaging said threaded bore of said implant and a post protruding above said first part, said second part including an outer surface with a tapered portion that tapers at an angle substantially the same as said predetermined angle for engaging said tapered surface of said first part.

35. The abutment of claim 34, wherein one of said two metallic pieces of said metallic core forms said tapered surface and the other of said two metallic pieces forms said socket.

36. The abutment of claim 34, wherein said metallic core engages a top surface of said implant adjacent to said boss.

37. An abutment for attaching to a dental implant embedded in living jawbone and having an upper surface with a fitting, said abutment comprising:

a tubular first part with a metallic core and a ceramic outer portion surrounding said metallic core, said tubular first part having a bore extending therethrough along a central axis, said bore including a tapered portion, said first part including a shoulder for supporting a dental prosthesis, said metallic core includes at least two separate metallic pieces; and an elongated second part for extending through said bore of said first part, said second part including a threaded stem for engaging a threaded bore of said implant and a post protruding above said first part, said post portion for supporting said dental prosthesis, said elongated second part including a tapered outer surface for engaging said tapered portion of said bore.

38. The abutment of claim 37, wherein one of said two metallic pieces of said metallic core forms said tapered surface and the other of said two metallic pieces forms said socket.

39. The abutment of claim 37, wherein said metallic core engages a top surface of said implant adjacent to said boss.

40. An abutment for attaching to a dental implant embedded in living jawbone and having an upper surface with a fitting, said abutment comprising:

a tubular first part with a metallic core and a ceramic outer portion surrounding said metallic core, said tubular first part having a bore extending therethrough along a central axis, said bore including a tapered portion tapering at an angle between about 5° and about 20°, said metallic core having a lower flanged portion for engaging said upper end of said implant;

an elongated part extending through said bore of said tubular first part and having a threaded stem for engaging a threaded bore of said implant and a post protruding above said first part, said elongated part including a tapered outer surface that tapers at said angle for forming a locking taper with said tubular first part; and a lubricant at an interface of said tapered outer surface and said tapered portion of said bore.

41. An abutment for supporting a dental prosthesis, said abutment being attached to a dental implant that is integrated with living jawbone, said dental implant including a threaded bore and a boss protruding away from an upper portion thereof, said abutment comprising:

a first part constructed of a metallic core and a ceramic outer piece positioned around said metallic core and attached thereto, said first part including a bore extending therethrough along a central axis and a socket for receiving said boss of said implant, said metallic core including at least two separate metallic pieces; and a second part for extending through said bore of said first part and holding said first part on said implant, said second part including a lower portion for threadably engaging said threaded bore of said implant and a head portion for engaging said first part in said bore.

42. The abutment of claim 41, wherein one of said two metallic pieces of said metallic core forms a portion of said bore and the other of said two metallic pieces forms said socket.

43. The abutment of claim 41, wherein one of said two metallic pieces engages a top surface of said implant adjacent to said boss.

44. The abutment of claim 41, wherein said bore is at least partially defined by a tapered surface that tapers inwardly at a predetermined angle with respect to said central axis in a direction toward said socket.

45. The abutment of claim 44, wherein one of said two metallic pieces of said metallic core forms said tapered surface of said bore.

46. The abutment of claim 41, wherein said post protrudes above said first part.

47. The abutment of claim 46, wherein said post protrudes above said first part by a distance that is larger than the height of said first part.

* * * * *